United States Patent [19]

Adams et al.

[11] 4,128,573
[45] Dec. 5, 1978

[54] 2-(SUBSTITUTED PHENYL)PROPIONIC ACIDS

[75] Inventors: Stewart S. Adams; Bernard J. Armitage; John S. Nicholson; James G. Tantum, all of Nottingham, England

[73] Assignee: Boots Pure Drug Company Limited, Nottingham, England

[21] Appl. No.: 725,645

[22] Filed: Sep. 22, 1976

Related U.S. Application Data

[63] Continuation of Ser. No. 488,739, Jul. 15, 1974, abandoned, which is a continuation of Ser. No. 123,034, Mar. 10, 1971, abandoned.

[30] Foreign Application Priority Data

Mar. 16, 1970 [GB] United Kingdom ............... 12570/70

[51] Int. Cl.$^2$ ............................................. C07C 69/76
[52] U.S. Cl. ............................... 562/465; 260/465 F; 260/559 D; 560/55; 424/308; 424/317; 562/444; 562/470; 568/637
[58] Field of Search ........... 260/473 R, 473 G, 520 C, 260/520 R; 560/55

[56] References Cited

U.S. PATENT DOCUMENTS 3,649,679  3/1972  Marshall ............................ 260/520

FOREIGN PATENT DOCUMENTS 916242  1/1963  United Kingdom .................... 260/473

Primary Examiner—Paul J. Killos
Attorney, Agent, or Firm—Hammond & Littell

[57] ABSTRACT

2-[4-(2-Fluorophenoxy)phenyl]propionic acid and salts, esters, the amide and the alcohol derived therefrom, useful as anti-inflammatory agents, and their preparation.

2 Claims, No Drawings

2-(SUBSTITUTED PHENYL)PROPIONIC ACIDS

This application is a continuation of Ser. No. 488,739, filed July 15, 1974, now abandoned, which in turn is a continuation of Ser. No. 123,034, filed Mar. 10, 1971, now abandoned.

This invention relates to 2-[4-(2-fluorophenoxy)-phenyl]propionic acid and salts, esters, the amide and the alcohol derived therefrom, which have been found to possess valuable biological properties.

According to one feature of the invention there are provided compounds of general formula I

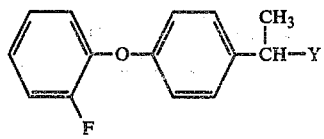

in which

Y is COOH, CONH$_2$ or CH$_2$OH; together with pharmaceutically acceptable esters, inorganic salts and organic salts of those compounds wherein Y is COOH.

Typical methods suitable for the preparation of the compounds of general formula I are as follows. Processes for the preparation of the stated starting materials and exact reaction conditions for the typical methods for the preparation of compounds of general formula I will be readily apparent to those skilled in the art from inherent knowledge, the prior art literature and the examples appended to this specification. As the methods are so-called "analogy processes" the descriptions have been kept brief and it is to be understood that any known procedures may be used to carry out the methods in addition to those procedures to which specific references are made.

In the following description the symbol R$_o$ is used to represent

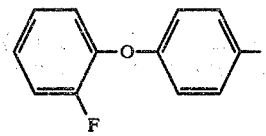

Acid

1. Hydrolysis of

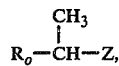

wherein Z is cyano, carbamoyl, N,N-disubstituted thiocarbamoyl, or COOR$_4$ in which R$_4$ is an ester-forming group, especially lower alkyl. The N,N-disubstituted thiocarbamoyl group is preferably derived from morpholine.

The hydrolysis may be carried out according to methods well-known in the art, for example by the use of acid or alkali in water, in an organic liquid reaction medium, or in a mixture thereof; a treatment temperature of 15°–150° C. is convenient. Preferably the hydrolysis is carried out by refluxing in the presence of an alkali metal hydroxide or of a mineral acid, and the organic liquid reaction medium is a lower alkanol.

The starting materials may be prepared, for example, from the substituted acetophenone R$_o$—CH—CH$_3$ by conventional means; other methods include the methods obtained below under the "Esters" and "Amides" headings below.

2. Decarboxylation of

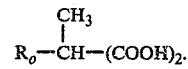

This may be carried out by heating the compound at about 200° C.

The starting material may be conveniently prepared in conventional manner, for example by reacting an alkyl ester of the acid R$_o$—CH$_2$—COOH with an alkyl carbonate and an alkali metal alkoxide to yield an alkali metal derivative of a compound of formula R$_o$—CH—(COOalkyl)$_2$, methylating this and hydrolysing the product.

3. Methylation of R$_o$—CH$_2$—COOH.

A metal (e.g. sodium) derivative of the acetic acid is used, prepared for example by reaction of the acid with an alkali metal amide (e.g. sodamide) in a suitable medium e.g. liquid ammonia. Conventional methylating agents may be used e.g. methyl iodide, dimethyl sulfate, and the like.

4. Oxidation of

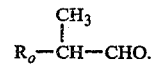

The oxidation may be carried out using any suitable oxidizing agent such as permanganates, chromic acid, dichromates, per acids, hydrogen peroxide, nitric acid, hypochlorites, silver oxide, or oxygen. A very convenient procedure involves oxidation in aqueous ethanol with alkali (e.g. an alkali metal hydroxide) and silver oxide.

The starting material may be prepared by the methods described for related compounds in our British patent specification No. 1,160,725.

5. Reductive cleavage of

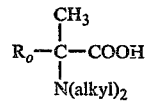

This may be achieved by conventional methods such as by catalytic hydrogenation e.g. using a palladium charcoal catalyst, or by treatment with sodium in liquid ammonia.

The starting material may be prepared by the methods described for related compounds in our British patent specification No. 1,167,192.

6. Hydrogenation of

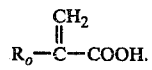

Typical procedures include hydrogenation over a conventional catalyst such as, for example, palladium, palladium oxide or platinum in an inert solvent such as a lower alkanol, benzene, toluene, xylene, tetrahydrofuran, dioxane and acetic acid, at a temperature of about 0° C. up to the reflux temperature of the system.

The starting material may be prepared conventionally such as for example, by the following reaction scheme:

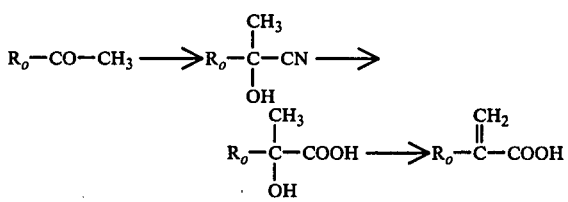

7. The reaction

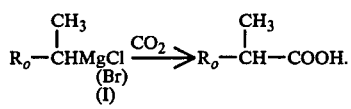

The Grignard reagent may be prepared conventionally by reaction of the appropriately substituted alkyl halide with magnesium in the presence of ether; it is then treated in ethereal solution with carbon dioxide and the additive compound so formed is decomposed with acid e.g. dilute sulfuric acid.

8. By means of the Ullmann reaction: i.e.

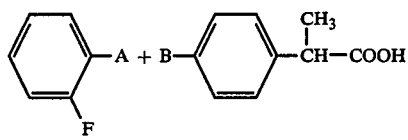

wherein one of A and B is OH and the other is halogen. Preferably A is OH and B is halogen.

This reaction is normally carried out by heating a metal derivative (e.g. an alkali metal derivative, especially potassium) of the hydroxy compound with the halogen compound (especially an iodo or bromo compound) at 100°–350° C. in the presence of a metal catalyst especially copper powder or copper bronze.

9. Hydrolysis of

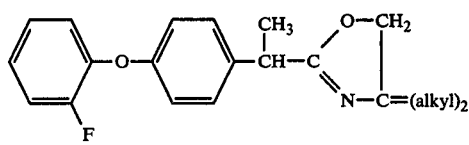

wherein "alkyl" is preferably methyl. Typical hydrolysis conditions are described under method (1).

The starting material may be prepared using procedures similar to those described by Meyers and Temple, J.A.C.S., 1970, 92, 6644.

10. Reaction of

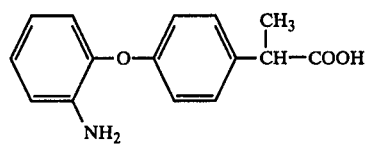

in known manner so as to convert the amino group to a fluorine atom. Examples of known procedures include the Schiemann reaction wherein the amino compound is diazotized in the presence of a fluorinating agent to form a fluorodiazonium derivative which is then decomposed by heating to give the corresponding fluoro compound. Suitable fluorinating agents include hydrogen fluoride, fluoboric acid, fluosilicic acid and phosphorus pentafluoride.

Esters

1. Esterification of the acid by conventional means:

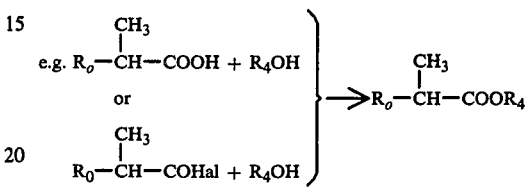

2. Alcoholysis of

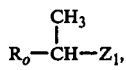

wherein $Z_1$ is cyano, carbamoyl, or N,N-disubstituted thiocarbamoyl (e.g. derived from morpholine).

3. By means of methods (3), (6), (8) and (10) as described under "Acid" but starting with the desired ester in place of the acid.

4. By alcoholysis of the oxazoline described under "Acid (9)".

Amides

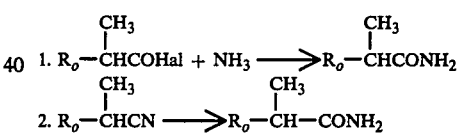

3. By means of methods (3), (6) or (10) as described under "Acid" but starting with the amide in place of the acid.

Salts

1. Reaction of the acid with organic or inorganic bases.

2. Alkaline hydrolysis of

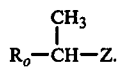

Alcohols

1. Reduction of the acid or, preferably, the esters (especially alkyl esters). The use of lithium aluminium hydride in a suitable solvent e.g. ether, followed by acidification, is one example. Alternatively hydrogenation in the presence of a cooper/chromium oxide catalyst may be used. Esters may be reduced with sodium in a lower alkanol.

2. By means of methods (8) or (10) as described under "Acid" but starting with a protected alcohol in place of the acid. The alcohol may be protected by a conventional readily removable group e.g. benzyl, which is finally removed after the earlier synthesis stages.

The compounds of general formula I possess anti-flammatory activity and are useful for the treatment of inflammatory conditions. They also possess analgesic and antipyretic properties and are useful for the treatment of conditions of pain and pyretic conditions. They are useful for the treatment of these three conditions individually or in any combination. Their activity has been determined in experimental animals using pharmacological tests which are known to be capable of characterizing compounds possessing the therapeutic properties of aspirin, namely anti-inflammatory, analgesic and antipyretic activity.

A preferred compound of the invention is that wherein Y is COOH. It is believed that when salts, esters, the amide or the alcohol derived from the acid are used in place of the acid said derivatives are metabolized by the animal body and are converted in the body into the corresponding acid.

It will be appreciated that, since the compounds of general formula I possess an asymmetric carbon atom, they are ordinarily present in the form of a racemic mixture. The resolution of such racemates may be carried out by any conventional method and the separated optically active stereoisomers form part of the present invention.

The compounds of the invention may be administered in the conventional manner of aspirin or usual manner for other anti-inflammatory, analgesic, and antipyretic agents, for example orally, topically, rectally or parenterally, preferably orally. The optimum dosage rate varies with the route of administration, but normally lies within the range 0.014–14.0 mg./kg./day, more usually between 0.35–7.0 mg./kg./day. The unit dose may vary from 1 mg. to 1000 mg. per subject; for oral administration the dosage rate is preferably 25–500 mg. per subject per day, optionally in divided doses.

In use, the compounds of the invention are administered in conventional formulations and accordingly the invention also provides therapeutic compositions which comprise a compound of the invention in association with pharmaceutical excipients for the production of compositions for oral, topical, rectal or parenteral administration. These compositions preferably contaon 0.1–90% by weight of a compound of the invention.

Compositions for oral administration are the preferred compositions of the invention, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus in the preparatin of tablets, typical excipients include disintegrating agents, e.g., corn starch and lubricating agents, e.g., magnesium stearate; in the preparation of capsules, standard gelatin capsules may be used containing the active ingredient alone or admixed with a diluent. The liquid compositions may comprise as excipients water and sucrose to provide syrups, water, dispersing agents and suspending agents, e.g., sodium carboxymethylcellulose to provide aqueous suspensions, and a non-toxic oil, e.g., a vegetable oil such as arachis oil and a suspending agent to provide oily suspensions.

Compositions for rectal administration are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1–4 carbon atoms which may contain a small proportion of water.

Compositions for parenteral administration are the conventional pharmaceutical forms for such administration, for example sterile suspensions in aqueous or oily media or sterile solutions in proplyene glycol.

In some formulations it may be beneficial to use the compounds of the invention in the form of particles of very small size, such as for example, as obtained by fluid energy milling, e.g., micronizing.

The invention further provides a method of treating inflammatory conditions, conditions of pain and pyretic conditions, individually or in any combination, which comprises administering a compound of the invention, preferably orally.

The products of the present invention may of course be employed in combination with other active anti-inflammatory agents, analgesics, and antipyretic agents, or with other drugs, as is already conventional in the art for other existing anti-inflammatory, analgesic and antipyretic materials such as aspirin.

The following non-limitative examples illustrate the invention.

EXAMPLE 1

2-Fluorophenol (2.35 g.) was fused with potassium hydroxide (1.7 g.) and a few drops of water by heating to 180° C. 2-(4-Iodophenyl)propionic acid (2.76 g.) and copper powder (0.1 g.) were then added and the melt ws heated at 160°–170° C. for 1 hour. The cooled solid was partitioned with methylene chloride (50 ml.) and 2.5N sodium hydroxide (50 ml.). The aqueous layer was acidified with hydrochloric acid, the resulting gum was extracted into ether, and the ether extract was extracted with saturated potassium carbonate solution. This aqueous extract was acidified with hydrochloric acid and the product isolated in ether. After evaporation the resulting solid was purified by preparative layer chromatography using 5% acetic acid/petroleum ether b.p. 62°–68° C. and eluting with ethyl acetate. Recrystallization from petroleum ether b.p. 62°–68° C. gave 2-[4-(2-fluorophenoxy)phenyl]propionic acid, m.p. 106°–108° C.

EXAMPLE 2

2-[4-(2-Fluorophenoxy)phenyl]propionic acid (2.32 g.) in ethanol (16 ml.) containing concentrated sulfuric acid (0.5 ml.) were refluxed for 5 hours and the alcohol removed. After dilution with water the product was isolated in ether and distilled to give ethyl 2-[4-(2-fluorophenoxy)phenyl]propionate, b.p. 176°–177° C./2.5 mm.

EXAMPLE 3

Ethyl 2-[4-(2-fluorophenoxy)phenyl]propionate (1.3 g.) in dry ether (5 ml.) was added dropwise to lithium aluminum hydride (200 mg.) in dry ether (5 ml.). After refluxing for 1 hour the excess hydride was decomposed with dilute sulfuric acid, and the ether layer was distilled to give 2-[4-(2-fluoropheoxy)phenyl]propanol, b.p. 178°–180° C./2.5 mm.

EXAMPLE 4

2-[4-(2-Fluorophenoxy)phenyl]propionic acid (0.2 g.) and thionyl chloride (1.5 ml.) were refluxed for 1 hour. Excess thionyl chloride was distilled and the residue was added to ammonium hydroxide (S.G. 0.88, 2 ml.) cooled in ice. The precipitate was collected and recrystallized from benzene/petroleum ether b.p. 60°–80° C. to give 2-[4-(2-fluorophenoxy)phenyl]propionamide, m.p. 106°–107.5° C.

EXAMPLE 5

2-[4-(2-Fluorophenoxy)phenyl]propionic acid (160 mg.) and benzylamine (72 mg.) were mixed in ether. The precipitated solid was recrystallized from alcohol/ether to give the benzylamine salt of 2-[4-(2-fluorophenoxy)phenyl]propionic acid, m.p. 122°–126° C.

EXAMPLE 6

No. 5 hard gelatin capsules were prepared each containing the following:

| (a) | 2-[4-(2-fluorophenoxy)phenyl]propionic acid | 5 mg. |
| | lactose | 95 mg. |
| (b) | 2-[4-(2-fluorophenoxy)phenyl]propionic acid | 5 mg. |
| | calcium phosphate | 5 mg. |
| | maize starch | 90 mg. |
| (c) | 2-[4-(2-fluorophenoxy)phenyl]propionic acid | 5 mg. |
| | corn starch \ | |
| | lactose  } equal parts by weight | 95 mg. |

-continued

| calcium phosphate | |

EXAMPLE 7

The following mixture (parts by weight) was formed into tablets in conventional manner, each tablet containing 5 mg. of active ingredient

| 2-[4-(2-fluorophenoxy)phenyl]propionic acid | 5 |
| --- | --- |
| corn starch | 30 |
| lactose | 163 |
| stearic acid | 1 |
| magnesium stearate | 1 |

Compositions similar to those described in Examples 6 and 7 were prepared containing as active ingredient other compounds of the invention described in Examples 1 – 5.

We claim:
1. A compound of the formula

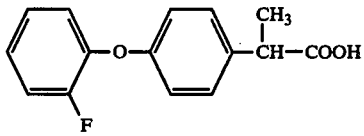

together with the pharmaceutically acceptable lower alkyl esters, inorganic salts and organic salts thereof.

2. 2-[4-(2-Fluorophenoxy)phenyl]propionic acid.

* * * * *